(12) United States Patent
Seifert et al.

(10) Patent No.: US 9,618,444 B2
(45) Date of Patent: Apr. 11, 2017

(54) VEHICLE MEASUREMENT SYSTEM

(75) Inventors: Wolfgang Seifert, Wielenbach (DE); Claudia Hofmann, Munich (DE)

(73) Assignee: ROBERT BOSCH GMBH, Stuttgart (DE)

( * ) Notice: Subject to any disclaimer, the term of this patent is extended or adjusted under 35 U.S.C. 154(b) by 0 days.

(21) Appl. No.: 13/985,156

(22) PCT Filed: Oct. 28, 2011

(86) PCT No.: PCT/EP2011/068957
§ 371 (c)(1),
(2), (4) Date: Sep. 30, 2013

(87) PCT Pub. No.: WO2012/113465
PCT Pub. Date: Aug. 30, 2012

(65) Prior Publication Data
US 2014/0021339 A1 Jan. 23, 2014

(30) Foreign Application Priority Data

Feb. 24, 2011 (DE) .......... 10 2011 004 663

(51) Int. Cl.
*G01N 21/17* (2006.01)
*G01B 11/25* (2006.01)
*G01B 5/00* (2006.01)

(52) U.S. Cl.
CPC .......... *G01N 21/17* (2013.01); *G01B 5/0025* (2013.01); *G01B 11/2513* (2013.01); *G01B 11/2545* (2013.01)

(58) Field of Classification Search
CPC .......... G01B 5/0025; G01B 11/2545; G01B 11/2513; G01B 11/25; G01N 21/17
See application file for complete search history.

(56) References Cited

U.S. PATENT DOCUMENTS

| 4,937,445 | A  | * | 6/1990  | Leong et al. | ............ | 250/237 G |
| RE34,749  | E  | * | 10/1994 | Leong et al. | ............ | 250/237 G |
| 6,205,243 | B1 |   | 3/2001  | Midgal et al. | | |
| 6,833,525 | B1 | * | 12/2004 | Clement et al. | ......... | 219/121.61 |
| 7,450,251 | B2 | * | 11/2008 | Liu et al. | ...................... | 356/625 |
| 8,400,494 | B2 | * | 3/2013  | Zalevsky et al. | ............... | 348/46 |
| 8,492,701 | B2 | * | 7/2013  | Nobis et al. | .................. | 250/221 |

(Continued)

FOREIGN PATENT DOCUMENTS

CN 2877948 3/2007
CN 201561741 U 8/2010

(Continued)

OTHER PUBLICATIONS

International Search Report for PCT/EP2011/068957, dated Mar. 1, 2012.

*Primary Examiner* — John Lee
(74) *Attorney, Agent, or Firm* — Gerard Messina

(57) ABSTRACT

A vehicle measurement system includes a laser projector which is designed to generate suitable laser radiation during the vehicle measurement operation, and a laser protection device which is suitable for protecting people and objects from the laser radiation. The laser projector and the laser protection device are designed as separate components and are combinable to form a laser projector having a laser protection device and are separable from one another again.

8 Claims, 6 Drawing Sheets

(56) References Cited

U.S. PATENT DOCUMENTS

| | | | |
|---|---|---|---|
| 2005/0121422 A1* | 6/2005 | Morden et al. | 219/121.6 |
| 2006/0244925 A1 | 11/2006 | Seki et al. | |
| 2008/0043409 A1 | 2/2008 | Kallabis | |
| 2008/0250585 A1 | 10/2008 | Auer et al. | |
| 2010/0060885 A1* | 3/2010 | Nobis et al. | 356/139.09 |
| 2010/0072180 A1* | 3/2010 | Schuermann et al. | 219/121.67 |
| 2010/0073461 A1* | 3/2010 | Hammes et al. | 348/42 |
| 2011/0058581 A1* | 3/2011 | Nobis et al. | 372/38.07 |
| 2012/0038934 A1* | 2/2012 | Miyasaka et al. | 356/610 |
| 2012/0218565 A1* | 8/2012 | Nobis et al. | 356/614 |
| 2014/0021339 A1* | 1/2014 | Seifert et al. | 250/216 |

FOREIGN PATENT DOCUMENTS

| | | |
|---|---|---|
| DE | 10 2006 002 794 | 7/2007 |
| DE | 20 2006 014 576 | 1/2008 |
| DE | 10 2007 021 328 | 11/2008 |
| DE | 10 2007 048 831 | 4/2009 |
| DE | 10 2009 029 234 | 3/2011 |
| DE | 102009029234 A1 | 3/2011 |
| EP | 0 668 236 | 8/1995 |
| EP | 2 071 279 | 6/2009 |
| WO | WO 2004/081488 | 9/2004 |
| WO | WO 2006/078684 | 7/2006 |

* cited by examiner

VEHICLE MEASUREMENT SYSTEM

BACKGROUND OF THE INVENTION

1. Field of the Invention

The present invention relates to a vehicle measurement system and in particular a vehicle measurement system having a laser projector and a laser protection device.

2. Description of the Related Art

It is known that laser projectors are used for vehicle measurement. Laser protection devices are necessary here for protecting against potentially hazardous laser radiation. These laser protection devices increase the size of the laser projectors, whereby they require additional space and are unwieldy to operate.

BRIEF SUMMARY OF THE INVENTION

One object of the present invention is to provide an improved laser vehicle measurement system, which is simple but nevertheless safe to handle.

A vehicle measurement system according to the present invention has a laser projector and a laser protection device. The laser projector is designed to generate laser radiation suitable for vehicle measurement during operation. The laser protection device is suitable for protecting people and objects from hazardous laser radiation generated by the laser projector. According to the present invention, the laser projector and the laser protection device are designed as separate components, which are combinable to form a functional unit of a laser projector and a laser protection device and are easily and in particular nondestructively separable from one another again.

Such a physical separation of the laser projector and the laser protection device (modularization) makes it possible to reduce the size of the vehicle measurement system for shipping, for example, and/or to combine the laser projector with different laser protection devices, in particular with laser protection devices having different dimensions, as a function of a laser projection image which is desired or to be generated. A laser protection device is preferably used which provides protection corresponding at least to laser protection class 1M according to DIN EN 60825-1.

Handling of the vehicle measurement system is simplified and the application range is increased by the possible variant formation.

In one specific embodiment, the system is designed in such a way that the laser projector may be operated only when combined with the laser protection device in such a way that the laser protection device is able to fulfill its intended purpose, which is to protect the surroundings around the laser projector from hazardous laser radiation. This increases safety during operation of the system since operation of the laser projector is reliably prevented when the laser protection device is not set up and functional as intended, so that people and/or objects may enter the vicinity of hazardous laser radiation.

In one specific embodiment, the laser projector has a laser beam source, a diffraction grating and a deflecting mirror or a deflecting prism, and the deflecting mirror or the deflecting prism is situated in such a way that a laser beam generated by the laser beam source is deflected by the deflecting mirror or by the deflecting prism onto the diffraction grating. Such a configuration of the laser beam source, the diffraction grating and the deflecting mirror or the deflecting prism permits a particularly compact design of the laser projector. The deflecting mirror or the deflecting prism may also be designed to be smaller than in the case in which the diffraction pattern generated by the diffraction grating is deflected.

In one specific embodiment, the laser protection device is mountable directly on the laser projector. The laser protection device may therefore be combined directly with the laser projector without any additional components, and a particularly compact vehicle measurement system may be implemented.

In one specific embodiment, the system additionally has at least one support ("stereo bar"), which is designed to accommodate the laser projector and at least one camera.

Through such a support, which is preferably designed to have torsional rigidity, a defined alignment of the laser projector and at least one camera are reliably established and high measuring accuracy is made possible. This also largely prevents errors due to temperature-related changes in length and/or twisting of the camera(s).

The support is preferably designed with mirror symmetry, so that the laser projector is situated in its central area and at least one camera is situated at each of its ends. The images recorded by the two cameras make it possible to measure the vehicle three-dimensionally with high precision.

In one specific embodiment, the laser protection device is mountable on the support. The support is a particularly stable fastening device for the laser protection device, which in this case may be designed to be particularly solid and stable.

If the laser protection device is mounted on the support, the laser projector may be replaced easily without having to dismantle the laser protection device itself. This simplifies the replacement of the laser projector, e.g., for repair and/or maintenance purposes, and reduces the risk of damage to the sensitive and expensive laser projector.

In one specific embodiment, the support itself is designed to assume the function of a laser protection device. The design of a system according to the present invention is thus simplified since a separate laser protection device, which is to be mounted on the laser projector or the support, may be dispensed with.

In one specific embodiment, the laser protection device has at least one mirror which is designed to deflect at least a portion of the laser radiation generated by the laser projector.

The mirror may be designed and situated in particular in such a way that it deflects a particularly hazardous portion of the laser radiation, in particular the main beam of the zero order of a laser diffraction pattern before it emerges from the laser protection device. A mirror situated in this way increases the safety of a vehicle measurement system according to the present invention since the emergence of hazardous laser radiation from the laser protection device is reliably prevented.

In one specific embodiment, the system additionally has a laser beam sensor, which is situated in such a way that the mirror reflects at least a portion of the laser radiation generated by the laser projector onto the laser beam sensor when the laser protection device is combined with the laser projector as intended. The mirror and the laser beam sensor are preferably situated in such a way that the main beam of the zero order of the laser diffraction pattern is reflected by the mirror onto the laser beam sensor.

By analyzing the signal of the laser beam sensor, it is possible to check on whether the laser protection device has been combined with the laser projector as intended. In particular, further operation of the laser projector may be prevented if the laser protection device is not set up as intended. This reliably prevents potentially hazardous operation of the laser projector with a laser protection device which has not been installed as intended and is not correctly aligned.

The laser beam sensor is preferably integrated into the laser projector to make available a compact device combining all electronic components.

In one specific embodiment, the reflective surface of the mirror is surrounded by a nonreflective edge. A mirror having a nonreflective edge achieves the result that a portion of the laser beam diffraction pattern, preferably the main beam of the zero order, is no longer reflected if it misses the center of the mirror on which the reflective surface of the mirror is formed and strikes an edge area of the mirror.

A faulty configuration or alignment of the laser protection device may thus be detected with the help of the laser beam sensor which detects the reflected portion of the laser beam diffraction pattern before the hazardous portion of the laser beam diffraction pattern has completely missed the mirror and emerges from the laser protection device.

In one specific embodiment, the laser protection device has at least one beam trap, which is designed for absorption of at least a portion of the laser radiation generated by the laser projector to prevent hazardous laser radiation from emerging from the laser protection device. The laser trap may be designed in particular in such a way that it absorbs the laser radiation reflected by the mirror.

DETAILED DESCRIPTION OF THE INVENTION

Figure 1:
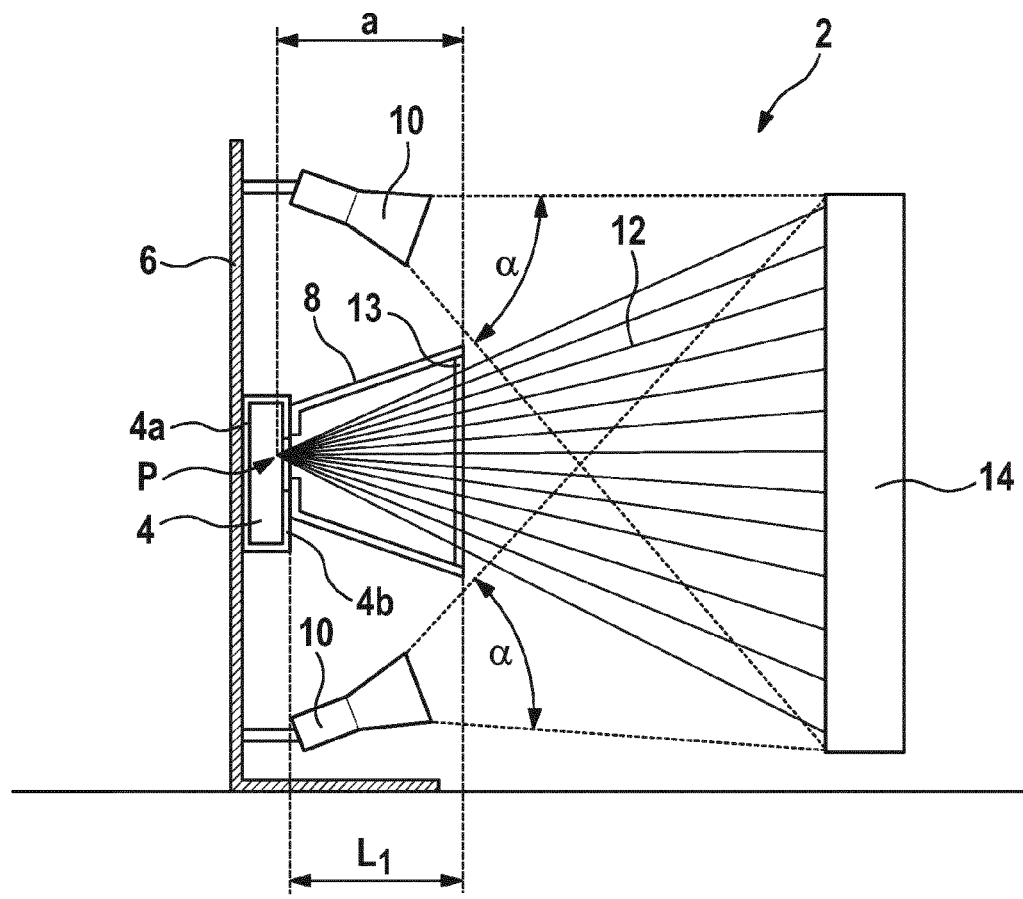
FIG. 1 shows a schematic top view of a vehicle measurement system according to the present invention in a first exemplary embodiment.

FIG. 1 shows a schematic top view of a vehicle measurement system 2 according to the present invention in a first exemplary embodiment.

System 2 has a laser projector 4, which is designed to generate laser radiation 12, in particular a laser beam diffraction pattern, during operation in order to irradiate an object 14 to be measured, e.g., the body of the vehicle, with a laser beam projection image.

Laser protection device 8 is situated in the area of laser projector 4, where laser radiation 12 emerges from laser projector 4, which is designed in such a way that it mechanically prevents people or objects from entering the area of concentrated and hazardous laser radiation 12 near laser projector 4.

Laser protection device 8 has a first overall length $L_1$ and is detachably attached to laser projector 4 in particular, so that laser projector 4 and laser protection device 8 may be transported and installed separately from one another. Laser projector 4 may be operated as needed, depending on the specific application, using a laser protection device 8 of a different design and in particular using laser protection devices 8 having different overall lengths $L_1$.

Laser projector 4 is attached to a support 6 ("stereo bar") with its rear side 4a facing away from laser protection device 8, the connection between laser projector 4 and support 6 being established in such a way that laser projector 4 and laser radiation 12 generated by laser projector 4 is alignable into a position suitable for the measurement.

On both sides of laser projector 4, a camera 10 is mounted on each side of support 6, each camera 10 having an image acquisition angle α, cameras 10 being aligned in such a way that the part to be measured of object 14 to be measured is located entirely within image acquisition angle α and is completely covered by cameras 10.

By recording and analyzing the image of laser radiation 12 projected onto measuring object 14 by two cameras 10 and reflected by measuring object 14, object 14 to be measured is accurately measurable.

Figure 2:
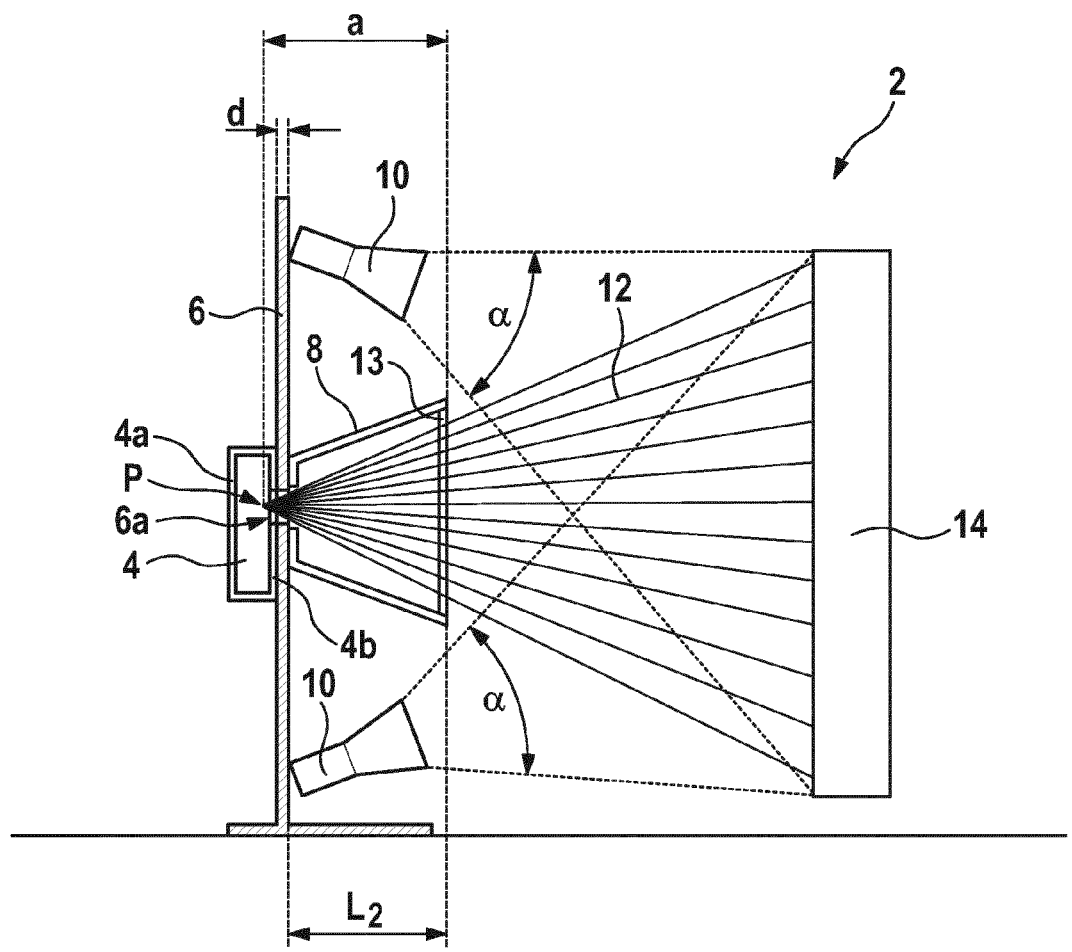
FIG. 2 shows a second exemplary embodiment of a vehicle measurement system according to the present invention.

FIG. 2 shows an alternative exemplary embodiment of a vehicle measurement system 2 according to the present invention. The features of system 2 which correspond to those of the first exemplary embodiment shown in FIG. 1 are labeled with the same reference numerals and are not described again in detail below.

System 2 according to the second exemplary embodiment differs from the system of the first exemplary embodiment shown in FIG. 1 in that laser projector 4 and laser protection device 8 are situated on different sides of support 6. In particular, laser projector 4 is attached at its front side 4b to support 6, where laser radiation 12 emerges from laser projector 4 during operation.

Support 6 has at least one opening 6a through which laser radiation 12 generated by laser projector 4 passes to strike object 14 to be measured through laser protection device 8 situated on the side of support 6 facing away from laser projector 4.

A system 2 according to the second exemplary embodiment is implementable in a particularly compact and space-saving design since both sides of support 6 are used for fastening laser projector 4 and laser protection device 8. In particular, system 2 may be implemented with a reduced overall length $L_2$ in comparison with the first exemplary embodiment since width d of support 6 increases the effective length of laser protection device 8, i.e., distance a between starting point P of laser radiation 12 and output side 13 of laser protection device 8 facing away from support 6. A laser protection device 8 of a shorter overall length $L_2$ than in the first exemplary embodiment may therefore be used without thereby reducing distance a between the starting point of laser radiation 12 and output side 13 of laser protection device 8. Such a system 2 having a reduced overall length $L_2$ may also be used particularly well in small workshops with little available space.

Figure 3:
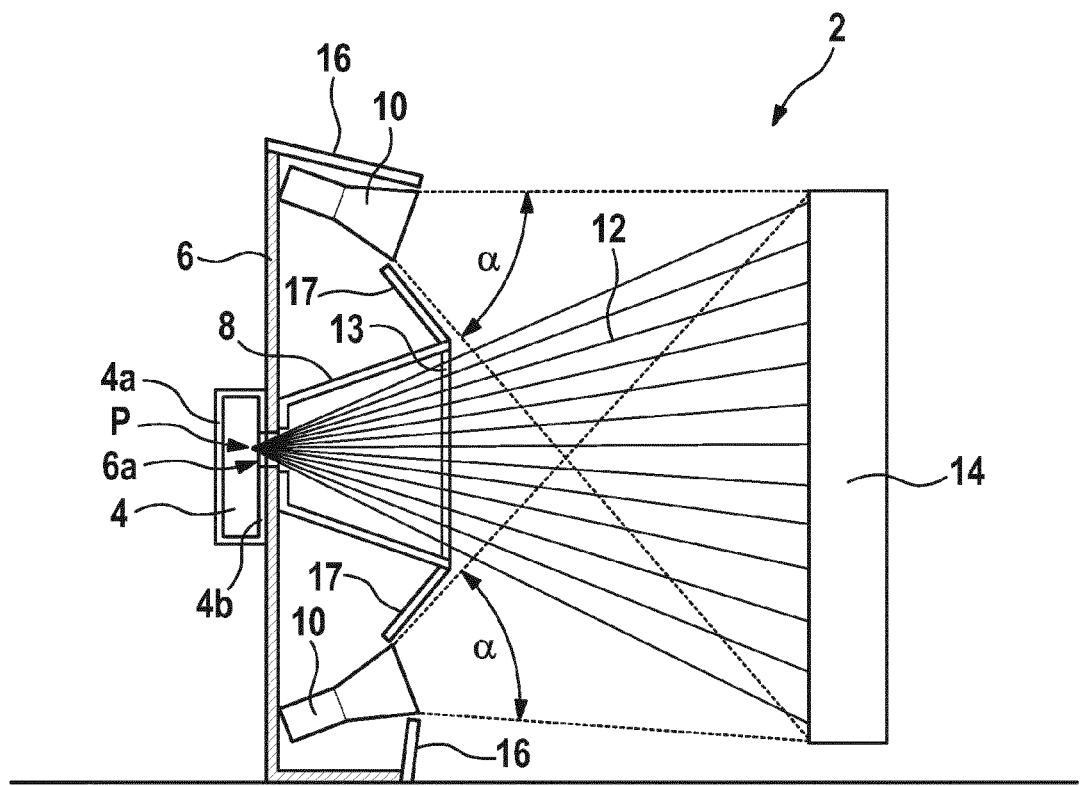
FIG. 3 shows a third exemplary embodiment of a vehicle measurement system according to the present invention.

FIG. 3 shows a third exemplary embodiment of a vehicle measurement system 2 according to the present invention, in which laser protection device 8 is designed with additional camera protection areas 16, 17.

Additional camera protection areas 16, 17 protect the sensitive cameras 10 from hazardous mechanical influences, e.g., jolts from the workshop area. In particular, camera protection areas 16, 17 prevent cameras 10 from becoming misaligned due to mechanical influences. Since misalignment of cameras 10 would result in false measuring results and would necessitate a complex readjustment of cameras 10, the accuracy and operational reliability of vehicle measurement system 2 is improved by such a laser protection device 8 having camera protection areas 16, 17.

Parts of camera protection areas 16, 17 may be designed to be pivotable or openable to permit access to cameras 10 as needed for adjustment, maintenance, cleaning or the like.

Figure 4:
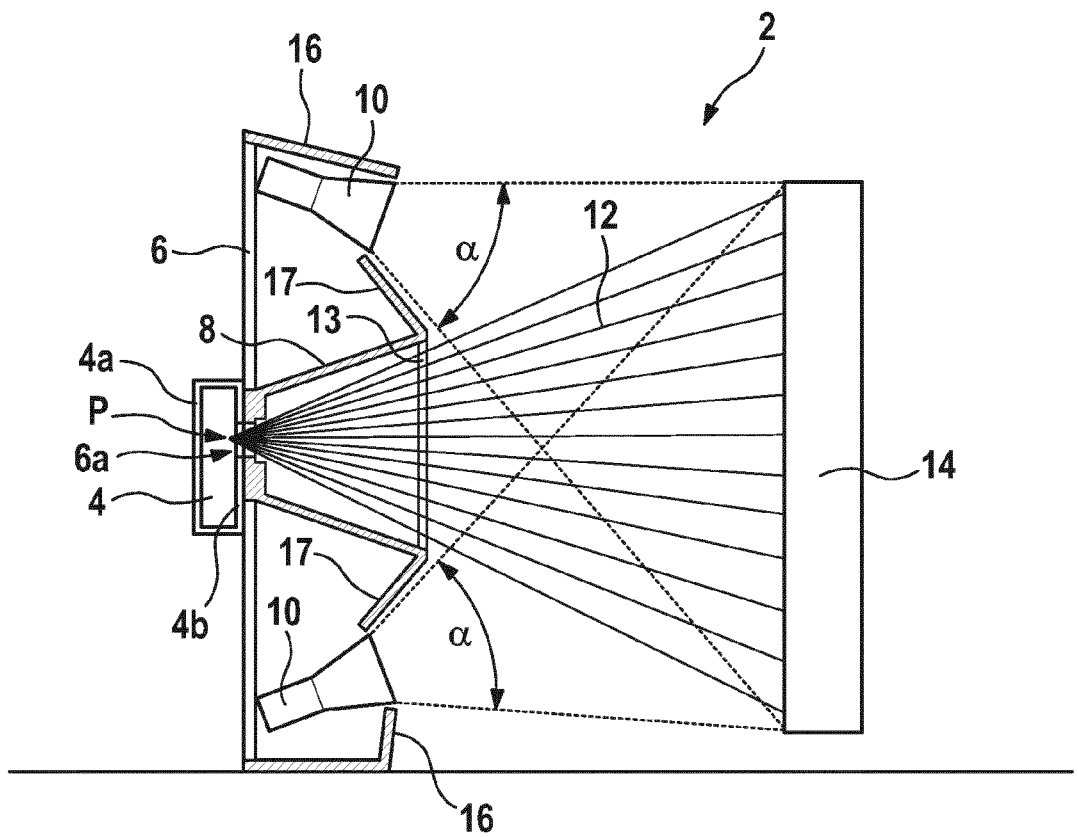
FIG. 4 shows a fourth exemplary embodiment of a vehicle measurement system according to the present invention.

FIG. 4 shows another exemplary embodiment of a vehicle measurement system 2 according to the present invention, in which both laser protection attachment 8 and camera protection areas 16, 17 are integrated into support 6, so that support 6 is designed as one piece, i.e., is integral with camera protection areas 16, 17 and a laser protection area 8. Such a one-piece, i.e., integral, design of support 6 makes it possible to design laser protection area 8 and camera protection areas 16, 17 to be particularly stable, so that they are also able to withstand massive mechanical influences in the workshop area.

Such an integral design of laser protection device 8 having support 6 is advantageous in particular if replacement of laser protection device 8 is not generally necessary. Replacement of laser projector 4 is also possible with no problem in this exemplary embodiment.

Figure 5:
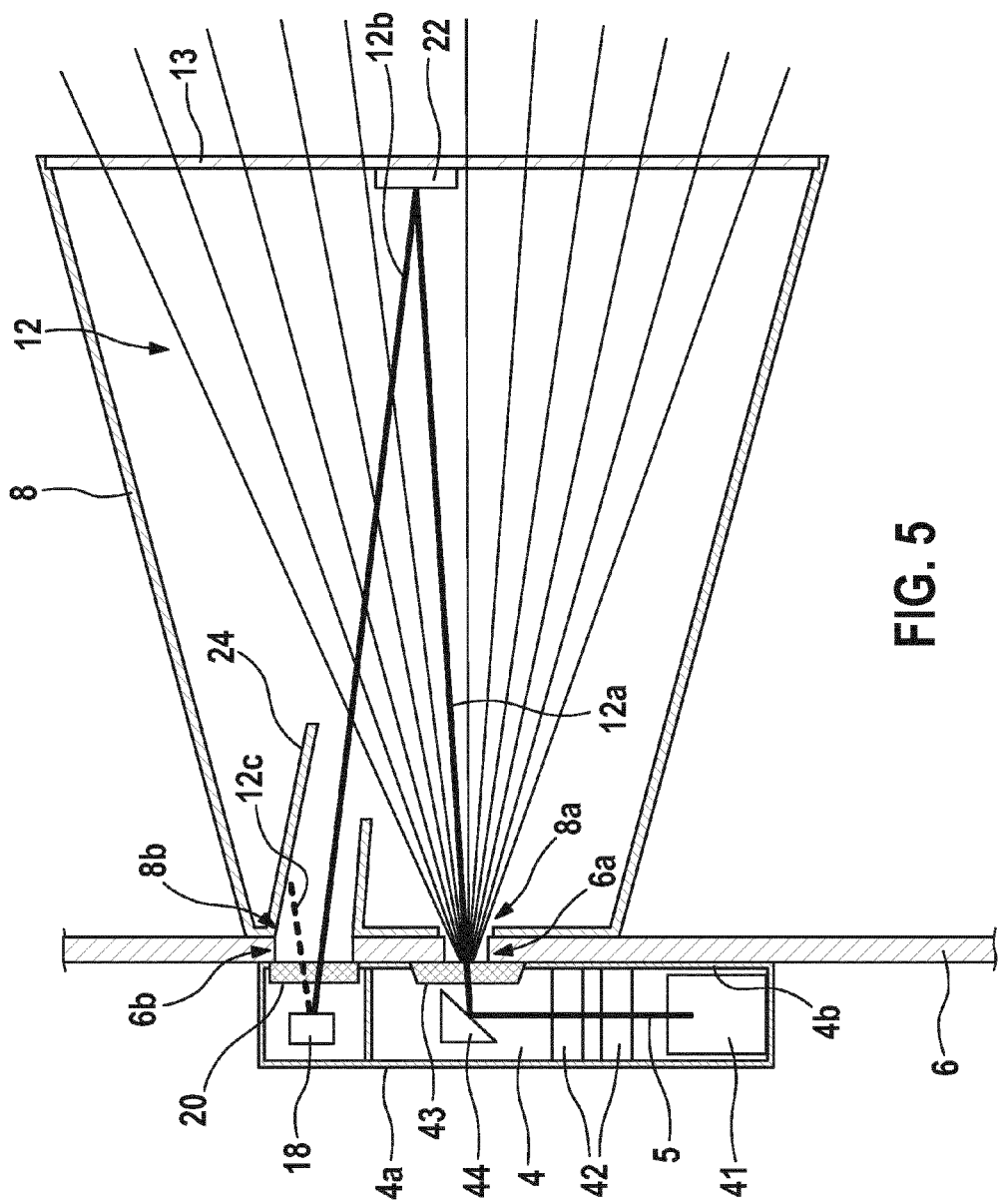
FIG. 5 shows an enlarged detailed diagram of an exemplary embodiment of a vehicle measurement system according to the present invention.

FIG. 5 shows an enlarged detailed diagram of an area of an exemplary embodiment of a system 2 according to the present invention having a laser projector 4 which is mounted on a support 6 and a laser protection device 8 mounted on the side of support 6 facing away from laser projector 4. Laser projector 4 has a laser diode 41, which is triggered by a suitable electronic system (not shown in FIG. 5) during operation to generate a laser beam 5.

Laser beam 5 passes through at least one lens system 42, which is situated in laser projector 4 and suitably shapes, i.e., focuses, laser beam 5. Laser beam 5 is deflected by a suitable deflecting mirror or a suitable deflecting prism 44 onto an optical grating 43 which, through optical refraction, creates a laser beam pattern 12 from laser beam 5 suitable for optical measurement.

Laser beam pattern 12 emerges from laser projector 4 through an opening formed on front side 4b in the housing of laser projector 4 and passes through a corresponding opening 6a formed in support 6 and through support 6 on which laser projector 4 is mounted.

A laser protection device 8, which is essentially funnel-shaped or cone-shaped or in the form of a truncated pyramid, is situated on the side of support 6 facing away from laser projector 4 and also has on its side facing support 6 an opening, which is aligned in such a way that laser beam pattern 12 emerging through opening 6a in support 6 is able to enter laser protection device 8. Laser protection device 8 is open or is provided with a protective disk which is permeable for the laser radiation on its output side 13 facing away from support 6 and from laser projector 4, so that laser beam pattern 12 is able to emerge from laser protection device 8 to strike object 14 to be measured (not shown in FIG. 5).

A mirror 22, which reflects central main beam 12a and thereby prevents the radiation-intensive and therefore potentially hazardous main beam 12a of laser beam pattern 12 from emerging from laser protection device 8, is situated in the area of the opening, i.e., the protective disk of laser protection device 8, which is struck by central main beam 12a of laser beam pattern 12 (diffraction beam of the zero order). Main beam 12a is reflected by mirror 22 back in the direction of laser projector 4 and of support 6.

At the location where reflected main beam 12b strikes the end of laser protection device 8 facing support 6, second openings 6b, 8b are formed in laser protection device 8 and support 6, which is situated behind it; reflected main beam 12b emerges from laser protection device 8 through these openings and through support 6 strikes a lens 20, which is situated behind support 6 and is designed as a Fresnel lens, for example. Lens 20 focuses reflected main beam 12b on a monitor diode 18 situated behind lens 20.

In the exemplary embodiment shown in FIG. 5, lens 20 and monitor diode 18 are integrated into laser projector 4. Monitor diode 18 and lens 20 may also be designed as separate devices independently of laser projector 4 and mounted on support 6.

The presence and the correct alignment of laser protection device 8 may be monitored by analyzing the signal output by monitor diode 18.

During operation, laser projector 4 is preferably operated initially at a reduced, harmless power level. If main beam 12a of laser radiation 12 is reflected by mirror 22 in such a way onto lens 20 and monitor diode 18 that monitor diode 18 outputs a signal at a predefined intensity, it is ensured that laser protection device 8 is correctly aligned with mirror 22 and that the power of laser projector 4 may also be increased to the power required to carry out the measurement.

On the other hand, laser projector 4 may be turned off and a warning signal may be output if the laser radiation detected by monitor diode 18 does not match a predefined value or if it differs by more than a predefined tolerance from the predefined value because laser protection device 8 is not correctly aligned, so that main beam 12a of laser radiation 12 is not projected onto monitor diode 18 as intended.

The safety of system 2 is further increased since a hazardous operation of laser projector 4 is prevented if laser protection device 8 is not correctly installed and aligned.

In addition, a beam trap 24, which absorbs laser radiation 12c which is reflected by lens 20 and/or monitor diode 18, is formed on laser protection device 8 to prevent uncontrolled emergence of reflected radiation 12c out of laser protection device 8, which could falsify the measuring results and/or could be a risk for the operator.

Figure 6:
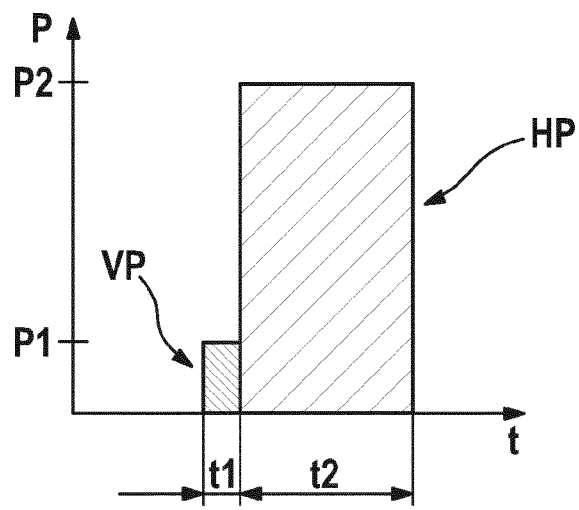
FIG. 6 shows the light output generated by the laser projector as a function of time in two different operating modes.

FIG. 6 shows a diagram in which light power P (y axis) emitted by laser projector 4 has been plotted as a function of time t (x axis).

Laser projector 4 is initially triggered with a prepulse VP at turn-on time t1, so that it generates a laser light pattern 12 using power P1 and turn-on time t1. A portion, preferably main beam 12a of laser light pattern 12 generated by prepulse VP, is reflected by mirror 22 and detected by monitor diode 18, as described previously in conjunction with FIG. 5.

If no malfunction is detected during analysis of the signal of monitor diode 18, i.e., if the intensity of laser light 12b detected and measured by monitor diode 18 is within a predefined range around a predefined setpoint value, then laser projector 4 is triggered with a main pulse HP which has a longer turn-on time t2, in such a way that it generates a laser light pattern 12 having a higher power P2 and a longer turn-on time t2. The actual measurement or projection is carried out using laser light pattern 12 generated by main pulse HP.

However, if the intensity of laser light 12b reflected onto it and ascertained by monitor diode 18 is outside of the predefined (tolerance) range during prepulse VP, then a malfunction is detected, and output of a main pulse HP to generate a laser light pattern 12 of an increased intensity P2 is prevented. Instead, a warning signal or error signal is output to instruct the user regarding the malfunction.

Due to the fact that before actual main pulse HP having a high power P2 and a longer turn-on time t2, a prepulse VP of a reduced power P1 in comparison with main pulse HP and a shorter turn-on time t1 is output initially and emission of a main pulse HP is reliably prevented when a malfunction is detected during detection and analysis of laser light pattern 12 generated by prepulse VP, the safety during operation of laser projector 4 is further increased since a malfunction of laser protection device 8 in particular is reliably detected and operation of laser projector 4, which would be hazardous for the operator, is prevented.

Figure 7:
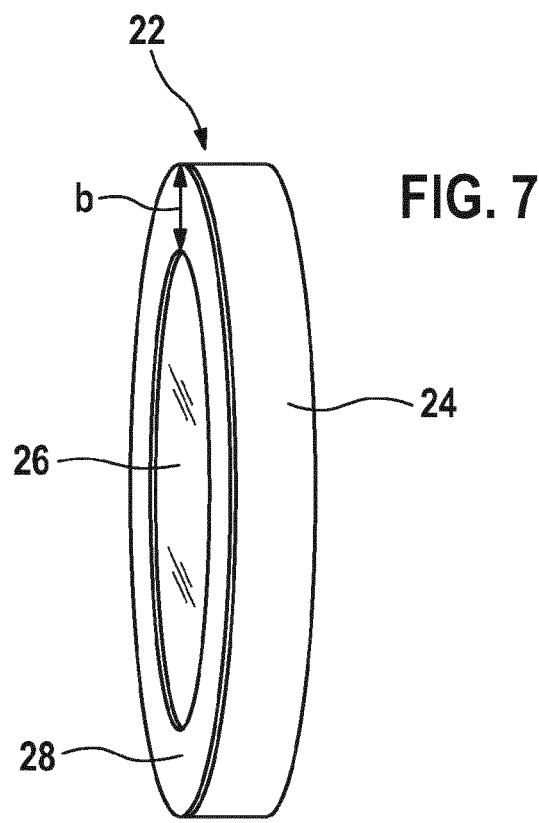
FIG. 7 shows a perspective view of a first exemplary embodiment of a mirror for use in a laser protection device according to the present invention.

FIG. 7 shows a perspective view of a first exemplary embodiment of a mirror 22, such as that mounted on the side of laser protection device 8 facing away from support 6 to reflect main beam 12a of diffraction pattern 12.

Mirror 22 according to the first exemplary embodiment is made of a preferably round disk having a mirror surface 26, which is designed to reflect main beam 12a of diffraction pattern 12. A ring 28 having a width b made of a nonreflective material is applied to mirror 24 around mirror surface 26, so that main beam 12a is not completely reflected when it strikes mirror 24 outside of central mirror surface 26. This ensures that monitor diode 18 will detect a drop in intensity of reflected laser beam 12b sufficient to shut down laser projector 4 before a portion of main beam 12a near mirror 22 emerges from laser protection device 8 in the event that laser protection device 8 is not correctly aligned. To ensure this, width b of ring 28 is preferably greater than the diameter of main beam 12a.

Alternatively, the mirror may also be designed as a disk 24 of an opaque nonreflective material to which a reflective material is applied in a central area 26 on at least one side to reflect laser radiation 12 and in particular main beam 12a of the diffraction pattern.

Figure 8:
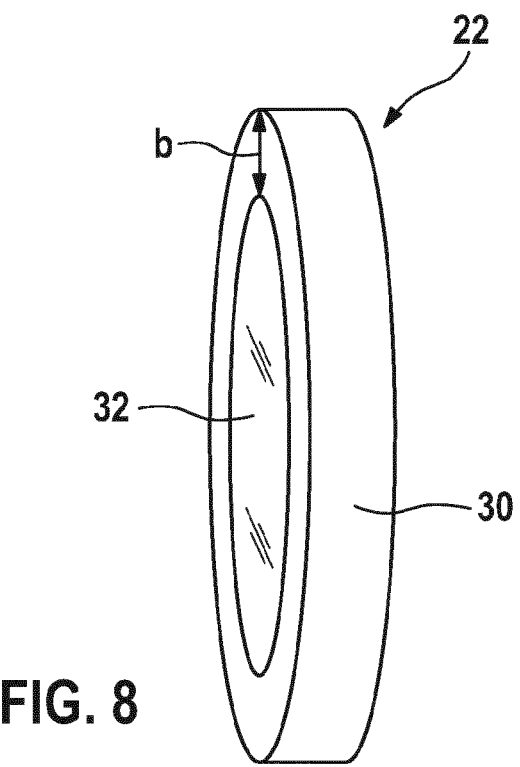
FIG. 8 shows a perspective view of a second exemplary embodiment of a mirror for use in a laser protection device according to the present invention.

FIG. 8 shows a second exemplary embodiment of a mirror 22. In this exemplary embodiment, mirror 22 is made up of a ring 30 of an opaque nonreflective material, and a light reflecting material 32 is introduced centrally into ring 30, so that mirror 22 has a central reflective area 32 on at least one of its end faces.

In designing mirror 22 and in particular the reflective and absorbent material, it should be noted that the remaining radiation transmission through reflective and opaque material 26, 28, 30, 32 is always less than the maximum value stipulated for laser protection to reliably prevent laser radiation of a hazardous intensity from emerging from laser protection device 8.

Those skilled in the art will recognize that the circular shape of mirror 22 shown in FIGS. 7 and 8 is not obligatory for the function described here. Mirror 22 may instead have any arbitrary shape as long as a central reflective area 26, 32 is surrounded by a nonreflective edge 28, 30.

What is claimed is:

1. A vehicle measurement system, comprising:
    a laser projector configured to generate laser radiation for vehicle measurement;
    a laser protection device configured to protect persons and objects from the laser radiation generated by the laser projector; and
    a laser beam sensor integrated into the laser projector;
    wherein the laser projector and the laser protection device are separate components which are configured to be (i) selectively attached to one another to form an integrated system and (ii) subsequently detached again,
    wherein the laser protection device has at least one mirror configured for deflecting at least one portion of the laser radiation generated by the laser projector, and
    wherein the at least one mirror reflects at least one portion of the laser radiation generated by the laser projector onto the laser beam sensor when the laser protection device is attached to the laser projector.

2. The system as recited in claim 1, wherein the laser projector is configured to be operable only when the laser projector is attached to the laser protection device.

3. The system as recited in claim 2, wherein the laser projector includes:
    a laser beam source;
    a diffraction grating; and
    one of a deflecting mirror or a deflecting prism positioned to deflect the laser beam generated by the laser beam source onto the diffraction grating.

4. The system as recited in claim 2, wherein the laser protection device is configured to be mountable directly on the laser projector.

5. The system as recited in claim 2, further comprising:
    a support configured to be mechanically connected to the laser projector and at least one camera.

6. The system as recited in claim 5, wherein one of (i) the laser protection device is configured to be mounted on the support, or (ii) at least a portion of the support forms the laser protection device.

7. The system as recited in claim 1, wherein the at least one mirror has a nonreflective edge.

8. The system as recited in claim 1, wherein the laser protection device has at least one beam trap configured to absorb at least a portion of the laser radiation generated by the laser projector.

* * * * *